United States Patent
Miyake

[11] Patent Number: 6,093,198
[45] Date of Patent: Jul. 25, 2000

[54] LACRIMAL PROBE

[76] Inventor: Masao Miyake, 1-13-20, Sakae-cho, Atsugi-shi, Kanagawa-ken, Japan

[21] Appl. No.: 08/969,586

[22] Filed: Nov. 13, 1997

[30] Foreign Application Priority Data

Oct. 27, 1997 [JP] Japan ..................................... 9-294614

[51] Int. Cl.⁷ ................................................. A61M 29/00
[52] U.S. Cl. ........................................... 606/190; 606/191
[58] Field of Search ................................ 606/190, 1, 192; 443/143

[56] References Cited

U.S. PATENT DOCUMENTS 5,021,043 6/1991 Becker et al. .......................... 606/192
5,169,314 12/1992 Long ....................................... 433/143
5,573,529 11/1996 Haak et al. ............................ 606/1

FOREIGN PATENT DOCUMENTS

T2619 of 1983 Japan.

*Primary Examiner*—Michael Buiz
*Assistant Examiner*—Jonathan Goldberg
*Attorney, Agent, or Firm*—Jacox Meckstroth & Jenkins

[57] ABSTRACT

The lacrimal probe 1 of the present invention comprising a tubular narrow holding member 2, and rods 3*a*, 3*b* which extend coaxially from both ends of the narrow holding member 2, being narrower than the narrow holding member 2. As a result, a lacrimal probe which is convenient to use, does not cause false ducts, and is difficult to bend, is obtained.

6 Claims, 1 Drawing Sheet

LACRIMAL PROBE

BACKGROUND OF THE INVENTION

1. Field of the Invention

The present invention relates to an ophthalmologic lacrimal probe. Moreover, the present specification is based on a Japanese Patent Application (Japanese Patent Application No. Hei 9-294614), and the content recited in said Application is incorporated as one part of the present specification.

2. Description of Related Art

Conventionally, the probe disclosed in JIS T 2619 as an ophthalmologic lacrimal probe is known. This lacrimal probe has rods of differing diameter attached coaxially to each end of a flat, narrow holding member, and is generally called a Bowman's probe. In addition, brass and silver, for example, are used as the material of the lacrimal probe.

This lacrimal probe is generally used in lacrimal duct formation. Concretely, the narrow holding member is held between the fingers, and the rod is inserted from the lacrimal punctum towards the canaliculus or the nasolacrimal duct, and by making a puncture, forms a lacrimal duct between the lacrimal punctum and the canaliculus or the nasolacrimal duct. In addition, depending on the need, a puncture can be made by changing the thickness of the inserted rod in sequence from a thin one to a thick one.

However, the above-described conventional lacrimal probe has, for example, the following problems:

(1) Because the narrow holding member is thin and flat, it is difficult to hold.

(2) When it is difficult to insert the lacrimal probe, if excess force is applied, the tip of the rod may puncture the mucous membrane, enter other tissue, and cause the formation of a false duct.

(3) When changing the thickness of the inserted rod from a thin one to thick, the thick rod may be difficult to insert.

(4) When the canaliculus is obstructed, it is difficult to distinguish by observation which part of the canaliculus is obstructed.

(5) Because the lacrimal probe is made of a relatively flexible metal such as brass or silver, when it encounters hard tissue, it may bend and be unable to puncture the tissue.

The aim of the present invention, in consideration of the above-mentioned conditions, is to provide a lacrimal probe that is convenient to use, and does not easily form false ducts or bend.

SUMMARY OF THE INVENTION

The present invention is an ophthalmologic lacrimal probe, characterized in comprising a tubular narrow holding member, and rods that extend coaxially from both ends of this narrow holding member, being narrower than the narrow holding member.

Additionally, the end of each rod is tapered towards the end, and it is preferable that there be a mark formed at a predetermined position from the ends of the rods. In this case, the mark should, for example, be formed at a position 10 mm from the ends of the rods. It is preferable that stainless steel be used as the material at least for the rods.

DESCRIPTION OF THE PREFERRED EMBODIMENT

Embodiment

Figure 1:
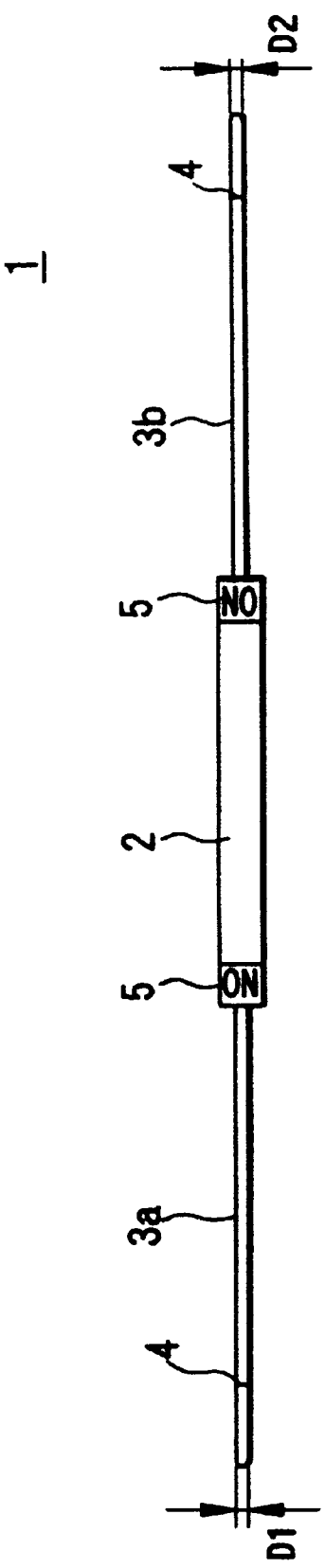
FIG. 1 is a drawing showing an example of the structure of the lacrimal probe of the present invention.

The embodiment of the present invention will be explained in the following based on the figure.

FIG. 1 shows an example of the structure of the lacrimal probe of the present invention. This lacrimal probe 1 is schematically formed from a tubular narrow holding member 2, and rods 3a, 3b which coaxially extend from the ends of the narrow holding member 2, and are narrower than narrow holding member 2.

For the rods 3a, 3b, ones of differing diameter are used, as in the above-described conventional lacrimal probe. The combination of diameters D1, D2 of the rods 3a, 3b are set, for example, as follows:

| probe number | diameter D1 (mm) of rod 3a | iameter D2 (mm) of rod 3b |
| --- | --- | --- |
| 0–0.1 | 0.45 | 0.50 |
| 0.2–0.3 | 0.55 | 0.60 |
| 0.4–0.5 | 0.65 | 0.70 |
| 0.6–0.7 | 0.75 | 0.80 |
| 0.8–0.9 | 0.90 | 1.00 |
| 1–2 | 1.10 | 1.20 |
| 3–4 | 1.30 | 1.40 |
| 5–6 | 1.50 | 1.60 |

The ends of the rods 3a, 3b are tapered towards the end within a range of 1 mm from the end, and as a result, the ends of the rods 3a, 3b have a diameter constricted one step narrower than the original diameter, that is, probe numbers 0.1–0.7 by 0.5 mm each, and probe numbers 0.8–6 by 1 mm each. Further, a mark 4 is imprinted at a position 10 mm from the end of the rods 3a, 3b.

At both ends of the narrow holding member 2, a probe number 5, corresponding to the diameter of the rods 3a, 3b, is imprinted. Additionally, stainless steel is used as the material for the lacrimal probe 1.

The method of using the lacrimal probe 1 having the above-described construction is fundamentally the same as that of the conventional lacrimal probe described above. That is, the narrow holding member 2 is held between the fingers, and the rods 3a, 3b are inserted towards the canaliculus or the nasolacrimal duct from the lacrimal punctum, and by making a puncture, a lacrimal duct is formed between the lacrimal punctum and the canaliculus or the nasolacrimal duct. In addition, as is necessary, the thickness of the inserted rods 3a, 3b can be changed in sequence from a thin one to a thicker one while performing the puncture.

The lacrimal probe 1 of the present invention has the following characteristics when compared to the above-described conventional lacrimal probe:

(1) Because the narrow holding member 2 is tubular, it is easy to hold and has superior operationality (it is easy to insert into the lacrimal punctum).

(2) Because the narrow holding member 2 is tubular, when the lacrimal probe 1 is difficult to insert, by lightly rotating the narrow holding member 2 with the fingers and inserting the rods 3a, 3b by a penetrating action, false ducts are not caused, and the rods 3a, 3b can be inserted in the original direction.

(3) Because the ends of the rods 3a, 3b have been constricted so as to equal the diameter of the rods 3a, 3b one step narrower, even when the thickness of the inserted rods 3a, 3b has been changed to one step thicker, the ends of the rods 3a, 3b can be easily inserted. Further, because the range of constriction of the diameter is only 1 mm from the end of the rods 3*a*, 3*b*, by continuing the insertion of rods 3*a*, 3*b*, the puncture area immediately expands to the original thickness of the rods 3*a*, 3*b*. Also, in the case of adults, because the distance from the lacrimal punctum to the vertical part of the superior and inferior canaliculi are both about 2.4 mm, it is also possible make the range of constriction of the diameter more than 1 mm from the ends of the rods 3*a*, 3*b*. However, in the present embodiment, in consideration of its pediatric use, the range of constriction is 1 mm from the end of the rods 3*a*, 3*b*.

(4) Because a mark 4 is imprinted at a position 10 mm from the end of the rods 3*a*, 3*b*, when there are lacrimal punctum obstructions, the obstructed areas of the lacrimal punctum can be easily estimated by their distance from the mark 4. Additionally, the reason the position of the mark 4 is 10 mm from the ends of the rods 3*a*, 3*b* is that the mark 4 will be visible if the position of the imprinting is 10 mm since in the case of adults the entire length of the superior lacrimal punctum is about 9.8 mm and that of the lower lacrimal punctum about 10.6 mm.

(5) Because stainless steel, which is rigid in comparison to the conventional lacrimal probe, is used as the material for the lacrimal probe 1, it will not bend even when it encounters hard tissue, and a puncture can be made in the tissue. This characteristic in particular can be exploited to good effect in the treatment of congenital nasolacrimal duct obstruction.

What is claimed is:

1. An ophthalmologic lacrimal probe comprising a tubular holding member and rods which extend coaxially from both ends of the holding member, said rods being narrower than the holding member, and the ends of said rods tapering toward the end so as to equal the diameter of the rods one step narrower.

2. A lacrimal probe according to claim 1 wherein a mark is formed at a predetermined position from the ends of said rods.

3. A lacrimal probe according to claim 2 wherein said mark is formed at a position 10 mm from the ends of said rods.

4. An ophthalmologic lacrimal probe comprising a tubular holding member and rods which extend coaxially from both ends of the holding member, said rods being narrower than the holding member, the ends of said rods tapering toward the end so as to equal the diameter of the rods one step narrower, and at least said rods being made of stainless steel.

5. A lacrimal probe according to claim 4 wherein a mark is formed at a predetermined position from the ends of said rods.

6. A lacrimal probe according to claim 5 wherein said mark is formed at a position 10 mm from the ends of said rods.

* * * * *